United States Patent
Sun

(10) Patent No.: US 6,187,983 B1
(45) Date of Patent: Feb. 13, 2001

(54) CONVERTING OXYGENATES TO OLEFINS IN THE PRESENCE OF ELECTROMAGNETIC ENERGY

(75) Inventor: Hsiang-ning Sun, Houston, TX (US)

(73) Assignee: Exxon Chemical Patents Inc, Houston, TX (US)

( * ) Notice: Under 35 U.S.C. 154(b), the term of this patent shall be extended for 0 days.

(21) Appl. No.: 09/069,635

(22) Filed: Apr. 29, 1998

(51) Int. Cl.$^7$ ............... C07C 1/20; C07C 1/207
(52) U.S. Cl. ............ 585/638; 585/639; 585/640; 585/641; 585/642; 204/157.15; 204/157.6
(58) Field of Search .................... 585/638, 639, 585/640, 641, 642; 204/157.15, 157.6

(56) References Cited

U.S. PATENT DOCUMENTS

| | | | |
|---|---|---|---|
| 4,279,722 * | 7/1981 | Kirkbride | 208/134 |
| 4,440,871 | 4/1984 | Lok et al. | 502/214 |
| 4,499,327 | 2/1985 | Kaiser | 585/640 |
| 4,849,573 * | 7/1989 | Kaeding | 585/640 |
| 4,861,938 | 8/1989 | Lewis et al. | 585/640 |
| 5,095,163 | 3/1992 | Barger | 585/640 |
| 5,126,308 | 6/1992 | Barger et al. | 502/214 |
| 5,191,141 | 3/1993 | Barger et al. | 585/640 |
| 5,215,634 * | 6/1993 | Wan et al. | 204/157.9 |
| 5,714,662 | 2/1998 | Vora et al. | 585/640 |
| 5,744,680 | 4/1998 | Mulvaney, III et al. | 585/640 |
| 6,046,373 * | 4/2000 | Sun | 585/640 |

FOREIGN PATENT DOCUMENTS

| | | |
|---|---|---|
| 2535119 * | 2/1976 | (DE) . |
| WO 93/24431 | 12/1993 | (WO) . |

OTHER PUBLICATIONS

Chang, "Methanol Conversion to Light Olefins," *Catal. Rev.–Sci. Eng.*, 26(3&4), pp. 323–345 (1984).
Kaeding, et al., "Production of Chemicals from Methanol," *Journal of Catalysts*, vol. 64, pp. 155–164 (1980).
*Zeolites*, vol. 17, pp 212–222 (1996).

* cited by examiner

*Primary Examiner*—Walter D. Griffin
(74) *Attorney, Agent, or Firm*—Linda Russell; Bradley Keller

(57) ABSTRACT

A process comprises contacting an oxygenate feed with a molecular sieve catalyst in the presence of an electromagnetic energy and converting the oxygenate feed to olefins.

38 Claims, No Drawings

CONVERTING OXYGENATES TO OLEFINS IN THE PRESENCE OF ELECTROMAGNETIC ENERGY

FIELD OF THE INVENTION

The present invention relates to a catalytic process of converting an oxygenate feed to olefins in the presence of an electromagnetic energy.

BACKGROUND OF THE INVENTION

Light olefins (defined herein as ethylene, propylene, butenes and mixtures thereof) serve as feeds for the production of numerous chemicals and polymers. Light olefins traditionally are produced by petroleum cracking. Due to the escalating cost of crude petroleum, efforts to develop light olefin production technologies based on alternative feedstocks have increased.

An important type of alternative feedstocks are oxygenates, such as alcohols, particularly methanol, dimethyl ether, dimethyl carbonate and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohols, alcohol derivatives, and other oxygenates have promise as an economical, non-petroleum source for olefin production.

Because olefins, particularly light olefins, are the most sought after products from oxygenate conversion and catalytic petroleum cracking processes, a continuing need exists for new catalysts, new ways of making known catalysts, and/or new processes to:

increase the yield of olefin products;

increase the yield of light olefin products;

reduce the yield of unwanted products such as heavy hydrocarbons having molecular weights heavier than butane or low-valued by-products like methane;

reduce coke formation;

increase catalyst performance—life, maintenance, activity, selectivity, stability; and regenerate spent catalyst more easily and/or more efficiently.

SUMMARY OF THE INVENTION

The present invention provides a process of contacting an oxygenate feed with a catalyst in the presence of electromagnetic energy at a sufficient power and under conditions effective to convert said oxygenate feed to a product comprising olefins.

DETAILED DESCRIPTION OF THE INVENTION

In the process of converting an oxygenate feed to olefins, it is desirable to increase the yield of and selectivity to olefins, reduce the production of byproducts, reduce coke formation, improve catalyst performance, and regenerate the spent catalyst more easily and/or more efficiently. The present invention provides a process of converting a oxygenate feed to olefins in the presence of electromagnetic energy. Many aspects of the oxygenate conversion process are improved.

Most catalysts that are used in oxygenate conversion and petroleum cracking processes are molecular-sieve containing catalysts. Molecular sieves generally comprise a stable crystalline framework structure enclosing cavities of molecular dimensions. The cavities form a well-defined microporous system of cages and one-, two- and/or three-dimensional channels. The channels may or may not be connected with one another. The cavities or pores in a given type of molecular sieve have well-defined dimensions which will only allow molecules up to a certain size to enter the pores. The pores can be as small as about 3 Angstroms and as large as about 15 Angstroms or larger. Most catalytic reactions are believed to take place inside of these pores.

The present invention should achieve many of the desired improvements by substantially any molecular sieve catalyst, regardless of the structure type or pore size. Preferred molecular sieve catalysts for use according to the present invention comprise "small" and "medium" pore molecular sieve catalysts. "Small pore" molecular sieve catalysts are defined as catalysts with pores having a diameter of less than about 5.0 Angstroms. "Medium pore" molecular sieve catalysts are defined as catalysts with pores having a diameter in the range of from about 5.0 to about 13.0 Angstroms.

A molecular sieve catalyst can be zeolitic or non-zeolitic. Zeolitic molecular sieve catalysts suitable for the use in the present invention with varying degree of effectiveness include, but are not necessarily limited to AEI, CHA, ERI, FAU, LOV, MON, RHO, THO, MFI, FER, AEL, MEL, and substituted examples of these structural types, as described in W. M. Meier and D. H. Olson, *Atlas of Zeolitic Structural Types* (Butterworth Heineman—3rd ed. 1997), incorporated herein by reference.

Preferred zeolite catalysts include but are not necessarily limited to zeolite A, zeolite X, zeolite Y, zeolite USY, ZSM-5, ZSM-11, ZSM-22, ZSM-34, MCM-41, erionite, chabazite, mordenite, zeolite L, zeolite beta, borosilicates and mixtures thereof.

Zeolites possess acidity as a result of the difference in valences between the two major framework elements—silicon (valence of 4+) and aluminum (valence of 3+). It is believed that zeolites can have both Lewis acid sites which accept electron donating moieties, and Bronsted acid sites which donate protons ($H^+$ ions). Most catalytic reactions take place at or near various acidic sites.

Zeolites may be used in the present invention as synthesized or the zeolites may be modified with a variety of modifiers or treatments. These modifiers may change the acidity, the nature of acid sites, pore size, pore size distribution, crystallinity, surface area, and other properties of the zeolites. Metal ions such as alkali metal ions, alkaline earth metal ions, transition metal ions, and ions of B, Ge, Sn, Ti, Zr, and others, can be incorporated into either the zeolite framework and/or outside the framework. Calcination, hydrothermal treatment, treatment with oxidizing and/or reducing agents, and treatment with acids such as HF, HCl, and chelating agents, also can be carried out to alter the physical and chemical properties of zeolites.

Non-zeolitic molecular sieves also are suitable for use in the present invention. Silicoaluminophosphates (SAPO's), metal aluminophosphates (MeAPO's), and metal aluminophosphosilicon oxides (MeAPSO's) have been synthesized and investigated as catalysts for converting oxygenate feeds or cracking heavy hydrocarbons to light olefins. Aluminophosphate molecular sieves (ALPO's) also may be used in the present invention too. These non-zeolitic molecular sieves collectively are referred to herein as "SAPO type" molecular sieves.

SAPO type molecular sieves have a three-dimensional microporous crystalline framework of $PO_2^+$, $AlO_2^-$, $SiO_2$ and MeO$_2$$^m$ tetrahedral units, with or without metals in the framework. The "m" superscript represents a net electric charge depending on the valence state of the metal, Me. When Me has valence state of +2, +3, +4, +5, or +6 valence state, m is −2, −1, 0, +1, and +2, respectively. "Me" includes, but is not necessarily limited to Zn, Mg, Mn, Co, Ni, Ga, Fe, Ti, Zr, Ge, Sn, Cr, and mixtures thereof.

Because an aluminophosphate (AlPO$_4$) framework inherently is neutral in electrical charges, the incorporation of silicon or other metallic or nonmetallic elements into the framework by substitution generates more active catalytic sites, particularly acid sites and increased acidity. Controlling the quantity and location of silicon atoms and other elements incorporated into an AlPO$_4$ framework is important in determining the catalytic properties of a particular SAPO type molecular sieve. Properly adjusted acid strength, acidity distribution, and acid site density are the keys to forming a good oxygenate conversion or petroleum cracking catalyst.

The catalytic properties can be modified after the SAPO type molecular sieve catalyst has been synthesized. "Post-synthesis" modification is accomplished by treating the molecular sieve with metallic, semi-metallic or non-metallic materials comprising nickel, cobalt, manganese, beryllium, magnesium, calcium, strontium, barium, lanthanides, actinides, fluorine, chlorine, chelating agents, and others. The modifiers may or may not become part of the final composition of the modified catalyst.

In the present invention, SAPO type molecular sieves suitable for converting an oxygenate feed to olefins include, but are not necessarily limited to SAPO-5, SAPO-11, SAPO-17, SAPO-18, SAPO-34, SAPO-44, SAPO-56 CoAPSO-34, NiAPSO-34, CoAPSO-17, NiAPSO-17, MnAPSO-17, CrAPSO's, MgAPSO's, CoAPO's, NiAPO's, MnAPO's, and mixtures thereof. MeAPO's and MeAPSO's may be synthesized as described in U.S. Pat. No. 5,126,308. SAPO-17, SAPO-34, and SAPO-44 may be synthesized according to U.S. Pat. No. 4,440,871, incorporated herein by reference, and *Zeolites*, Vol. 17, pp 512–522 (1996), incorporated herein by reference.

Small pores—pores smaller than about 5 Angstroms—are believed to favor light olefins production as a result of sieving effects. A preferred SAPO type molecular sieve is SAPO-34 which has a pore diameter of about 4.3 Angstroms. Other preferred small pore SAPO type molecular sieves include, but are not necessarily limited to SAPO-17, SAPO-18, SAPO-44, CoAPSO-17, NiAPSO-17, MnAPSO-17, CoAPSO-34, NiAPSO-34, CrAPSO-34, and mixtures thereof. Light olefins are preferred products when small pore SAPO molecular sieve catalysts are used.

For the chabazite-like or erionite-like SAPO-17, SAPO-18, SAPO-34 and SAPO-44 molecular sieves, it may be possible to incorporate more silicon atoms into the tetrahedral positions of the framework to afford greater flexibility in adjusting their acidic properties. Medium pore molecular sieves such as SAPO-11 and large pore molecular sieves such as SAPO-5 produce less light olefins and more heavier hydrocarbons, including aromatics.

In the present invention, molecular sieve catalysts are used to convert oxygenate feeds to olefins in the presence of an electromagnetic energy. An electromagnetic energy is suitable for use in the invention as long as the energy comprises a proper frequency and a sufficient power. The oxygen feed is converted at a desired conversion in the presence of the electromagnetic energy under conditions effective to reach a desired selectivity of olefins.

A preferred electromagnetic energy comprises a frequency in a microwave region. A "microwave energy" source should have a frequency in the range of from about 10 MHz to about 50,000 MHz, more preferably in the range of from about 100 MHz to about 30,000 MHz. The electromagnetic energy sources preferably should have a power in the range of from about 0.01 W to about 100,000 W, preferably in the range of from about 1.0 W to about 1,000 W.

In the present invention, more than one electromagnetic energies having the same or different frequencies/powers may be applied simultaneously or not simultaneously. When the electromagnetic energies are not applied simultaneously, they are applied preferably in series or consecutively. The electromagnetic energies may be applied to different segments or regions of the reactor simultaneously or consecutively. In addition, the electromagnetic energy may be applied in various modes—pulsing, continuous, semicontinuous, intermittent, or a combination thereof.

The time periods of applying the electromagnetic energies depend on the frequencies and the powers of the electromagnetic energies, the mode of application, the catalyst used, the composition of the oxygenated feed, the space velocity, temperature, pressure, and other reaction conditions. For each application, the time period generally is in the range of from about 0.01 seconds to about 240 minutes, preferably from about 0.1 seconds to about 120 minutes.

In another embodiment of the present invention, one or more electromagnetic energies are applied to the molecular sieve catalyst itself prior to contacting the oxygenate feed with the catalyst. In this case, the time period of applying the electromagnetic energies depends on the frequencies and the powers of the electromagnetic energies, the catalyst, the oxygenated feed, temperature, pressure, and other reaction conditions. The time period generally is in the range of from about 0.01 seconds to about 120 minutes.

The process for converting oxygenate feeds to olefins employs an organic starting material (feedstock) preferably comprising "oxygenates." As used herein, the term "oxygenates" or "oxygenate feed" is defined to include, but not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety preferably should contain in the range of from about 1 to about 10 carbon atoms and more preferably in the range of from about 1 to about 4 carbon atoms.

Representative oxygenates include, but are not necessarily limited to, lower straight chain or branched aliphatic alcohols, their unsaturated counterparts, their esters, and their nitrogen, halogen and sulfur analogues. Examples of suitable compounds include, but are not necessarily limited to: methanol; ethanol; n-propanol; 2-propanol; nbutanol, sec-butanol, t-butanol, isobutanol, $C_5$–$C_{10}$ alcohols; $C_2$–$C_{10}$ aliphatic diols; methyl ethyl ether; dimethyl ether; diethyl ether; di-isopropyl ether; dimethyl sulfide; diethyl sulfide; methyl mercaptan, ethyl mercaptan; methylamine; dimethylamine, trimethylamine, ethylamine; diethylamine, triethylamine, methyl bromide, ethyl bromide, methyl chloride, ethyl chloride; methyl iodide, ethyl iodide, formaldehyde; di-methyl carbonate; di-methyl ketone; n-alkyl amines, n-alkyl halides, n-alkyl sulfides having n-alkyl groups of comprising the range of from about 3 to about 10 carbon atoms; and mixtures thereof. As used herein, the term "oxygenate" designates only the organic material used as the feed. The total charge of feed to the reaction zone may contain additional compounds such as diluents.

A preferred oxygenate comprises a compound selected from the group consisting of methanol, dimethyl ether, dimethyl carbonate, methyl formate, and mixtures thereof.

Preferably, the oxygenate feedstock should be contacted in the vapor, liquid, or supercritical state phase in a reaction zone with the defined molecular sieve catalyst at effective process conditions so as to produce the desired olefins, i.e., an effective temperature, pressure, WHSV (Weight Hourly Space Velocity) and, optionally, an effective amount of diluent, correlated to produce olefins. Alternately, the process may be carried out in a liquid or a mixed vapor/liquid phase. When the process is carried out in the liquid phase or a mixed vapor/liquid phase, different conversions and selectivities of feedstock-to-product may result depending upon the catalyst and reaction conditions.

The temperature employed in the conversion process may vary over a wide range depending, at least in part, on the selected catalyst. Although not limited to a particular temperature, best results will be obtained if the process is conducted at temperatures in the range of from about 100° C. to about 700° C., preferably in the range of from about 150° C. to about 650° C., and most preferably in the range of from about 200° C. to about 600° C. Lower temperatures generally result in lower rates of reaction, and the formation of the desired light olefin products may become markedly slow. However, at higher temperatures, the process may not form an optimum amount of light olefin products, and the coking rate may become too high.

Olefin products, particularly light olefins, will form—although not necessarily in optimum amounts—at a wide range of pressures, including but not limited to autogeneous pressures and pressures needed to maintain a super critical state. The pressures generally are in the range of from about 10 Pa to about 500 MPa. A preferred pressure is in the range of from about 1.0 kPa to about 17 MPa, most preferably in the range of from about 50 kPa to about 5 MPa. The foregoing pressures are exclusive of diluent, if any is present, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins such as ethylene still may form.

When the oxygenate feed comprises mainly alcohols, ethers may become the preferred products under conditions not effective to produce olefins.

The process should be continued for a period of time sufficient to produce the desired olefin products under the reaction conditions. The reaction time may vary from hundredths of a second to a few hours. The reaction time is largely determined by the reaction temperature, the pressure, the catalyst selected, the weight hourly space velocity, the reaction phase (liquid or vapor), the frequency and power of the electromagnetic energy, the number of electromagnetic energies, the manner the electromagnetic energies are applied, and the selected process design characteristics.

A wide range of weight hourly space velocities (WHSV), defined as weight feed per hour per weight of catalyst, for the feedstock will function in the present invention. The WHSV generally should be in the range of from about 0.01 $hr^{-1}$ to about 5000 $hr^{-1}$, preferably in the range of from about 0.05 $hr^{-1}$ to about 2500 $hr^{-1}$, and most preferably in the range of from about 0.1 $hr^{-1}$ to about 1000 $hr^{-1}$. The catalyst may contain other materials which act as inerts, fillers, or binders; therefore, the WHSV is calculated on the weight basis of oxygenate feed and catalyst.

The inerts, fillers, or binders contained in the catalyst may be selected from a large number of suitable materials. Some materials may serve more than one purpose. SiC and silicon nitride may be used to enhance the absorption of an electromagnetic energy and facilitate heat transfer. Quartz can be used to reflect electromagnetic energy. Aluminas, silicas, and phosphates may be used as binders to strengthen the particle integrity.

One or more diluents may be fed to the reaction zone with the oxygenate feeds, such that the total feed mixture comprises diluent in a range of from about 1 mol % and about 99 mol %. Diluents which may be employed in the process include, but are not necessarily limited to, helium, neon, argon, krypton, nitrogen, carbon monoxide, carbon dioxide, water (as steam under some reaction conditions), hydrogen, long-chain paraffins, other hydrocarbons (such as methane and ethane, etc.), aromatic compounds, and mixtures thereof. Preferred diluents are water and nitrogen.

An embodiment of a reactor system for the present invention includes but is not necessarily limited to a fluidized bed, a circulating fluid bed reactor with continuous regeneration, a riser, a fixed bed and a moving bed. A resonant cavity type device can be used. The reactor may be equipped with an inner concentric tube made of material transparent to microwave and the space between the tube and the reactor is filled with loose microwave reflecting material. The catalyst is placed inside the inner tube. Other types of design which focus the electromagnetic energy on the desired area within the reactor can also be used.

Many different materials are suitable for constructing the oxygenate conversion reactor. Preferably, the reactor is made of a material that does not absorb or interfere with the electromagnetic energy significantly. Preferred materials include, but are not necessarily limited to glass, ceramics, and poly(tetrafluoroethylene) such as Teflon®. Conventional carbon steel or stainless steel reactors also may be used by proper designs to minimize interactions between the reactor and the electromagnetic energy.

The reactor may be provided further with a suitable lining or packing material that would reflect or focus the electromagnetic energy to the desired region. A suitable material is Poly(tetrafluoroethylene) such as Teflon® when the reaction temperature does not exceed about 350° C. Polyetheretherketone (PEEK) is another material suitable for use as liner. Quartz and silicon carbide are two other materials that may be used for liners or packing materials. More than one material may be used at the same time.

The invention will be better understood with reference to the following examples which are intended to illustrate, but not to limit the present invention.

EXAMPLE I

A 5.0 gram of SAPO-34 molecular sieve catalyst of −16+20 mesh particle size is mixed with 15.0 grams of SiC of −16+20 mesh particle size to form a uniform mixture. This catalyst mixture is placed in a quartz reactor. A nitrogen gas at 50 ml/min is used to purge air out of the reactor while the catalyst is heated to 250° C. at a rate of 5° C. per minute. After one hour of purging, a pure methanol feed is pumped into the reactor with an ISCO® pump at a WHSV of about 0.5 $h^{-1}$ through a preheat zone filled with quartz beads only and maintained at a temperature of 230° C. The reactor pressure is maintained at slightly higher than atmospheric pressure. A continuous electromagnetic energy is simultaneously applied to the reactor and catalyst. The electromagnetic energy has a frequency of about 2450 MHz and a power of about 100 watts.

The products in the effluent are analyzed by on-line gas chromatographs equipped with both thermal conductivity and flame ionization detectors. The conversion of methanol is found to be 95%. The combined selectivity of ethylene, propylene, and butenes (light olefins) exceeds 90 wt % (excluding water).

EXAMPLE II

Example I is repeated except that SAPO-34 is replaced with SAPO-17. The initial reactor temperature is maintained at 300° C. Analyses of the effluents show that methanol conversion is nearly quantitative and the combined selectivity of light olefins exceeds 90 wt % (excluding water).

EXAMPLE III

A 5.0 gram of SAPO-34 molecular sieve catalyst of −16+20 mesh particle size is mixed with 15.0 grams of silica of −16+20 mesh particle size to form a uniform mixture. This catalyst mixture is placed in a Teflon® concentric tube inside a tubular ceramic reactor. Quartz particles in −20+50 mesh size are used to fill the space between the tube and the reactor wall. A nitrogen gas at 50 ml/min is used to purge air out of the entire reactor while the catalyst is heated to 200° C. at a rate of 5° C. per minute. After one hour of purging, a 4:1 (molar ratio) water-methanol mixture feed is pumped into the reactor with an ISCO® pump at a WHSV of about 0.5 $h^{-1}$ through a preheat zone filled with quartz beads only and maintained at a temperature of 190° C. The reactor pressure is maintained at slightly higher than ambient atmospheric pressure. A continuous electromagnetic energy is simultaneously applied to the reactor and catalyst. The electromagnetic energy has a first frequency of about 2450 MHz and a power of about 100 watts, and a second frequency of about 1700 MHz and a power of about 40 watts.

The products in the effluents are analyzed by on-line gas chromatographs equipped with both thermal conductivity and flame ionization detectors. The conversion of methanol is found to be 100%. The combined selectivity of ethylene, propylene, and butenes exceeds 95 wt % (excluding water).

EXAMPLE IV

An experiment similar to EXAMPLE I is carried out except that 5.0 grams of ZSM-34 molecular sieve are used as the catalyst to replace the SAPO-34 catalyst.

Analyses of the effluents show that methanol conversion is about 90% and the combined selectivity to light olefins is about 80 wt % (excluding water).

EXAMPLE V

An experiment similar to EXAMPLE I is carried out except that 5.0 grams of ZSM-5 with a silicon-to-aluminum atomic ratio of 280 are used as the catalyst to replace the SAPO-34 catalyst.

Analyses of the effluents show that methanol conversion is over 95% and the combined selectivity of $C_2$–$C_6$ olefins is about 65 wt % (excluding water).

From the results of the examples, it can be concluded that high oxygenate conversions and high selectivities to olefins can be achieved by using the process of the present invention—contacting an oxygenate feed with a molecular sieve catalyst in the presence of an electromagnetic energy of sufficient power.

Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

I claim:

1. A process for converting an oxygenate feed to an olefin product comprising: contacting the oxygenate feed with a molecular sieve catalyst in a reaction system, and applying electromagnetic energy to the reaction system at conditions effective to convert the oxygenate feed to a product, the product comprising an olefin.

2. The process of claim 1 wherein said molecular sieve comprises a zeolite.

3. The process of claim 1 wherein said molecular sieve comprises a non-zeolitic molecular sieve.

4. The process of claim 1 wherein said catalyst comprises a material selected from the group consisting of ZSM-5, ZSM-11, ZSM-22, ZSM-34, silicalite, mordenite, chabazite, erionite, zeolite X, zeolite Y, zeolite USY, zeolite L, zeolite beta, MCM-41, borosilicates and mixtures thereof.

5. The process of claim 1 wherein said catalyst comprises a silicoaluminophosphate (SAPO).

6. The process of claim 5 wherein said SAPO is selected from the group consisting of SAPO-5, SAPO-11, SAPO-17, SAPO-18, SAPO-34, SAPO-44, SAPO-56, and mixtures thereof.

7. The process of claim 1 wherein said catalyst is selected from the group consisting of SAPO-17, SAPO-18, SAPO-34, SAPO-44, CoAPSO-17, CoAPSO-34, NiAPSO-17, NiAPSO-34, MnAPSO-17 and mixtures thereof.

8. The process of claim 1 wherein said catalyst comprises a molecular sieve selected from the group consisting of MeAPO, MeAPSO, ALPO, and mixtures thereof.

9. The process of claim 1 wherein said catalyst is selected from the group consisting of ZSM-5, ZSM-34, chabazite, erionite, and mixtures thereof.

10. The process of claim 1 wherein said oxygenate feed is selected from the group consisting of methanol, ethanol, n-propanol, 2-propanol, dimethyl carbonate, dimethyl ether, methylethyl ether, diethyl ether, n-butanol, sec-butanol, t-butanol, isobutanol, methyl formate, methyl acetate, ethyl formate, ethyl, acetate, methyl chloride, ethyl chloride, methyl bromide, ethyl bromide, methyl iodide, ethyl iodide, methyl mercaptan, dimethyl sulfide, methylamine, dimethylamine, trimethylamine, ethylamine, diethylamine, triethylamine, and mixtures thereof.

11. The process of claim 1 wherein said oxygenate feed further comprises a diluent.

12. The process of claim 11 wherein said diluent is selected from the group consisting of water, nitrogen, hydrogen, carbon monoxide, carbon dioxide, helium, argon, methane, ethane, and mixtures thereof.

13. The process of claim 1 wherein said electromagnetic energy comprises a frequency in the range of from about 10 to about 50,000 MHz.

14. The process of claim 13 wherein said frequency is in the range of from about 100 MHz to about 30,000 MHz.

15. The process of claim 1 wherein the electromagnetic energy is applied at a power in the range of from about 1 to about 1000 watts.

16. The process of claim 1 wherein said electromagnetic energy comprises from about two to about ten frequencies simultaneously.

17. The process of claim 1 wherein said electromagnetic energy comprises from about two to about ten frequencies not simultaneously.

18. The process of claim 1 wherein said conditions comprise a temperature in the range of from about 150° C. to about 650° C., a pressure in the range of from about 10 Pa to about 500 MPa, and a weight hourly space velocity of from about 0.01 hr$^{-1}$ to about 5000 hr$^{-1}$.

19. The process of claim 1 wherein the product comprises light olefins.

20. The process of claim 1 wherein the reaction system includes a reactor equipped with an inner tube made of material transparent to microwave.

21. A process for converting an oxygenate feed to an olefin product comprising:
    contacting the oxygenate feed with a SAPO catalyst in a reaction system;
    applying electromagnetic energy to the reaction system at conditions effective to convert the oxygenate feed to an olefin product, wherein the electromagnetic energy is applied at a frequency in the range of from about 10 to about 50,000 MHz and a power in the range of from about 10 watts to about 500 watts.

22. The process of 21 wherein said conditions comprise a temperature in the range of from about 150° C. to about 650° C., a pressure in the range of from about 10 Pa to about 500 MPa, and a weight hourly space velocity of from about 0.01 hr$^{-1}$ to about 5000 hr$^{-1}$.

23. The process of claim 22 wherein the olefin product comprises light olefins.

24. The process of claim 21 wherein said SAPO is selected from the group consisting of SAPO-5, SAPO-11, SAPO-17, SAPO-18, SAPO-34, SAPO-44, SAPO-56 and mixtures thereof.

25. The process of claim 24 wherein the olefin product comprises light olefins.

26. The process of claim 21 wherein said oxygenate feed further comprises a diluent selected from the group consisting of water, nitrogen, hydrogen, carbon monoxide, carbon dioxide, helium, argon, methane, ethane, and mixtures thereof.

27. The process of claim 21 wherein said oxygenate feed is selected from the group consisting of methanol, ethanol, n-propanol, 2-propanol, dimethyl carbonate, dimethyl ether, methylethyl ether, diethyl ether, n-butanol, sec-butanol, t-butanol, isobutanol, methyl formate, methyl acetate, ethyl formate, ethyl, acetate, methyl chloride, ethyl chloride, methyl bromide, ethyl bromide, methyl iodide, ethyl iodide, methyl mercaptan, dimethyl sulfide, methylamine, dimethylamine, trimethylamine, ethylamine, diethylamine, triethylamine, and mixtures thereof.

28. The process of claim 21 wherein said electromagnetic energy further comprises from about one to about nine additional frequencies in the range of 10 MHz to about 50,000 MHz.

29. The process of claim 21 wherein the reaction system includes a reactor equipped with an inner tube made of material transparent to microwave.

30. A process for converting an oxygenate feed to an olefin product comprising:
    contacting the oxygenate feed with a zeolite catalyst in a reaction system;
    applying electromagnetic energy to the reaction system at conditions effective to convert the oxygenate feed to an olefin product, wherein the electromagnetic energy is applied at a frequency in the range of from about 10 to about 50,000 MHz and a power in the range of from about 10 watts to about 500 watts.

31. The process of 30 wherein said conditions comprise a temperature in the range of from about 150° C. to about 650° C., a pressure in the range of from about 10 Pa to about 500 Mpa, and a weight hourly space velocity of from about 0.01 hr$^{-1}$ to about 5000 hr$^{-1}$.

32. The process of claim 30 wherein said zeolite is selected from the group consisting of ZSM-5, ZSM-34, chabazite, erionite, and mixtures thereof.

33. The process of claim 32 wherein the olefin product comprises light olefins.

34. The process of claim 30 wherein the olefin product comprises light olefins.

35. The process of claim 30 wherein said oxygenate feed further comprises a diluent selected from the group consisting of water, nitrogen, hydrogen, carbon monoxide, carbon dioxide, helium, argon, methane, ethane, and mixtures thereof.

36. The process of claim 30 wherein said oxygenate feed is selected from the group consisting of methanol, ethanol, n-propanol, 2-propanol, dimethyl carbonate, dimethyl ether, methylethyl ether, diethyl ether, n-butanol, sec-butanol, t-butanol, iso-butanol, methyl formate, methyl acetate, ethyl formate, ethyl, acetate, methyl chloride, ethyl chloride, methyl bromide, ethyl bromide, methyl iodide, ethyl iodide, methyl mercaptan, dimethyl sulfide, methylamine, dimethylamine, trimethylamine, ethylamine, diethylamine, triethylamine, and mixtures thereof.

37. The process of claim 30 wherein said electromagnetic energy further comprises from about one to about nine additional frequencies in the range from about 10 MHz to about 50,000 MHz.

38. The process of claim 30 wherein the reaction system includes a reactor equipped with an inner tube made of material transparent to microwave.

* * * * *